United States Patent [19]
Ott et al.

[11] 3,966,938
[45] June 29, 1976

[54] TREATMENT OF THROMBOSIS AND THE INHIBITION OF BLOOD PLATELET AGGREGATION

[75] Inventors: Hans Ott, Pfeffingen; Rudolf Suess, Bettingen, both of Switzerland

[73] Assignee: Sandoz Ltd., Basel, Switzerland

[22] Filed: May 8, 1975

[21] Appl. No.: 575,523

Related U.S. Application Data

[60] Division of Ser. No. 408,053, Oct. 19, 1973, Pat. No. 3,899,494, which is a continuation-in-part of Ser. No. 305,289, Nov. 10, 1972, abandoned, which is a continuation-in-part of Ser. No. 303,069, Nov. 2, 1972, abandoned, which is a continuation-in-part of Ser. No. 140,239, May 4, 1971, abandoned.

[30] Foreign Application Priority Data

| Oct. 26, 1972 | Switzerland | 15675/72 |
| Oct. 26, 1972 | Switzerland | 15676/72 |
| Oct. 26, 1972 | Switzerland | 15677/72 |
| Oct. 26, 1972 | Switzerland | 15678/72 |

[52] U.S. Cl. ............................................. 424/258
[51] Int. Cl.² ........................................ A61K 31/47
[58] Field of Search ................................. 424/258

*Primary Examiner*—Stanley J. Friedman
*Attorney, Agent, or Firm*—Gerald D. Sharkin; Robert S. Honor; Thomas O. McGovern

[57] ABSTRACT

The invention concerns new 4a,10b-cis-substituted benzo-naphthyridines of the formula:

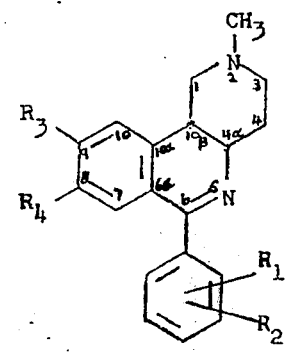

wherein
  $R_1$ is hydrogen, alkyl, alkoxy, alkylthio, fluorine, chlorine, bromine, nitro, trifluoromethyl, amino or acylamino,
  $R_2$ is hydrogen, chlorine, alkyl or alkoxy, and
  $R_3$ and $R_4$ are both hydrogen or both methoxy, or $R_3$ and $R_4$ together are methylenedioxy.

A process for the production thereof and intermediates therefor are also described.

The compounds inhibit blood platelet aggregation.

20 Claims, No Drawings

TREATMENT OF THROMBOSIS AND THE INHIBITION OF BLOOD PLATELET AGGREGATION

This application is a division of U.S. Pat. application, Ser. No. 408,053, filed Oct. 19, 1973, which issued as U.S. Pat. No. 3,899,494 on Aug. 12, 1975, which in turn is a continuation-in-part of U.S. Pat. application, Ser. No. 305,289, filed Nov. 10, 1972, now abandoned, which in turn is a continuation-in-part of U.S. Pat. application, Ser. No. 303,069, filed Nov. 2, 1972, now abandoned, which in turn is a continuation-in-part of U.S. Pat. application, Ser. No. 140,239, filed May 4, 1971, now abandoned.

In accordance with the invention, there is provided new 4a,10b-cis-substituted benzo-naphthyridines of formula I,

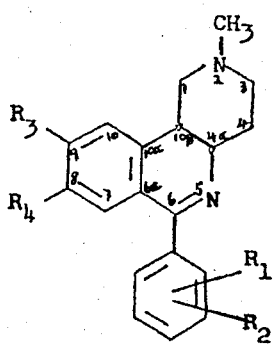

wherein
$R_1$ is hydrogen, alkyl of 1 to 3 carbon atoms, alkoxy of 1 to 3 carbon atoms or alkylthio of 1 to 3 carbon atoms, fluorine, bromine, chlorine, nitro, trifluoromethyl, amino or acylamino, wherein the acyl group is selected from;
  aliphatic acyl of 1 to 18 carbon atoms, benzoyl, benzoyl wherein the benzene ring is substituted by radicals X and Y, X being lower alkyl of 1 to 4 carbon atoms, lower alkoxy of 1 to 4 carbon atoms, fluorine, chlorine or bromine, and Y being hydrogen, lower alkyl of 1 to 4 carbon atoms, lower alkoxy of 1 to 4 carbon atoms, or chlorine,
  phenyl-alkenoyl, wherein the alkylene section has 1 to 3 carbon atoms, cinnamoyl, phenyl-alkenoyl as defined above or cinnamoyl which are substituted in the benzene ring by radicals X and Y which are as defined above, or the radical A—CO—, A being a 5- or 6-membered heterocyclic aromatic ring containing an oxygen, nitrogen or sulfur atom,
$R_2$ is hydrogen, chlorine, alkyl of 1 to 3 carbon atoms or alkoxy of 1 to 3 carbon atoms, and
$R_3$ and $R_4$ are both hydrogen or both methoxy, or
$R_3$ and $R_4$ together are methylenedioxy,
and pharmaceutically acceptable acid addition salts thereof.

It will be appreciated that the acyl moiety of acylamino may be regarded as —CO—R.

When the radical R is alkyl of up to 17 carbon atoms, this may, for example, signify butyl, tert.butyl, pentyl, octyl, undecyl or heptadecyl. This radical preferably contains 4 to 8 carbon atoms.

When R is a 5- or 6-membered heteroaromatic ring containing a hetero atom of the series oxygen, nitrogen or sulphur, and bound to the carbonyl group with a carbon atom, this especially signifies furyl, thienyl or pyridyl, preferably 2-furyl, 2-thienyl or 3-pyridyl.

Alkylene in phenylalkylene especially contains 1 or 2 carbon atoms and preferably signifies methylene.

When the radicals X and/or Y are alkyl or alkoxy of 1 or 2 carbon atoms and preferably signify methyl or methoxy.

When R is an aromatic group, this preferably signifies phenyl, styryl or benzyl substituted by X' and Y', wherein X' is hydrogen, methyl, methoxy, fluorine, chlorine or bromine, and Y' is hydrogen, methyl or methoxy.

The radical R—CONH— is preferably in the 4 position of the phenyl radical to which it is bound.

A class is provided of compounds of formula,

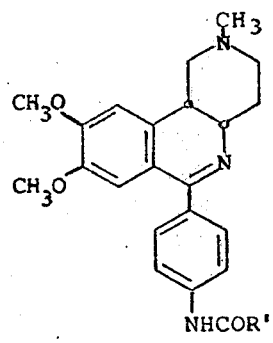

wherein
R' is hydrogen, isopropyl, alkyl of 4 to 8 carbon atoms, furyl, thienyl or pyridyl, or phenyl, styryl or benzyl substituted by X' and Y', as defined above.

The compounds wherein R' is hydrogen are especially interesting.

Further, in accordance with the invention a compound of formula I is obtained by a process comprising
a. cyclizing, with an acid water-removing condensation agent, a 3,4-cis-substituted compound of formula II,

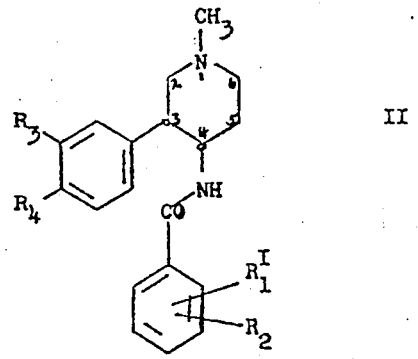

where
$R_2$, $R_3$ and $R_4$ are as defined above, and
$R_1{}^I$ is hydrogen, alkyl of 1 to 3 carbon atoms, alkoxy of 1 to 3 carbon atoms or alkylthio of 1 to 3 carbon atoms, fluorine, chlorine, bromine, nitro or trifluoromethyl, to obtain a compound of formula Ia,

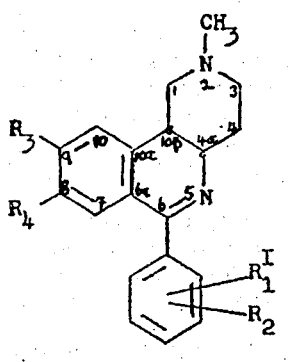

Ia wherein $R_1'$, $R_2$, $R_3$ and $R_4$ are as defined above,
b. reducing a compound of formula Ib,

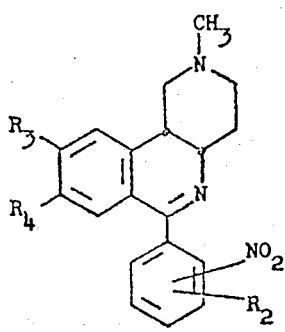

Ib wherein $R_2$, $R_3$ and $R_4$ are as defined above, to obtain a compound of formula Ic,

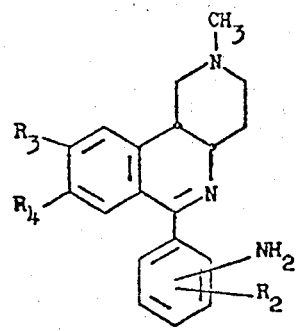

Ic wherein $R_2$, $R_3$ and $R_4$ are as defined above, or
c. acylating a compound of formula Ic to obtain a compound of formula Id,

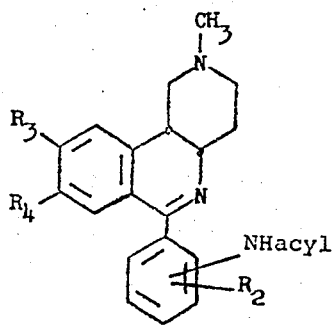

Id wherein $R_2$, $R_3$ and $R_4$ and acyl are as defined above.

The resulting compound of formula I may be isolated in the form of a free base or as an acid addition salt thereof.

The cyclization of process variant a) is a Bischler-Napieralski reaction and is suitably effected by heating on amide of formula II with an excess of phosphorus oxychloride for some time, e.g. for 1 to 10 hours, at a temperature from 60°C to the boiling temperature of the reaction mixture. The ring closure may also be effected using phosphorus oxychloride or phosphorus pentoxide in the presence of an inert solvent, e.g. a chlorinated hydrocarbon such as chloroform, or in a cyclic hydrocarbon such as benzene, toluene, xylene or tetraline, at an elevated temperature, preferably at the boiling temperature of the reaction mixture.

Other reagents which are especially suitable for the cyclization are polyphosphoric acid or phosphorus pentachloride.

The cyclization does not change the steric arrangement of the substituents on the piperidine ring, so that the stereochemistry in positions 4a and 10b (ring linkage) of the resulting 1,2,3,4,4a,10b-hexahydro-benzo[c][1,6]naphthyridine derivatives of formula I agrees with that of the starting materials.

The reduction of the nitro group in the compounds of formula Ib in process variant (b), may, for example, be effected with iron turnings and an acid such as dilute hydrochloric acid. If desired an inert solvent, e.g. a lower alcohol such as ethanol, may be used. The reaction is suitably carried out at an elevated temperature, e.g. at the boiling temperature of the reaction mmixture.

Process variant (c) is effected in conventional manner by treating the amino derivatives of formula Ic with an acylating agent, e.g. formic acid or a carboxylic acid chloride or anhydride, optionally in an inert solvent and at an elevated temperature.

The compounds of formula I may be isolated and purified in accordance with known methods.

The compounds of formula II may, for example, be obtained by reacting a compound of formula III,

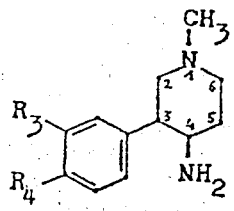

III wherein
$R_3$ and $R_4$ are as defined above,
and which is cis-substituted in the 3,4-position, with a compound of formula IV,

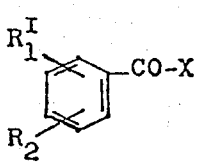

IV wherein
$R_1'$ and $R_2$ are as defined above, and
X is chlorine or bromine, preferably chlorine.

This reaction may be effected in an aqueous solution in the presence of an alkali metal hydroxide (Schotten-Baumann process) or in an inert organic solvent, e.g. a cyclic ether such as dioxane, in the presence of a tertiary organic base such as pyridine or triethylamine.

The compounds of formula III may, for example, be produced as follows:

A phenylacetic acid of formula V,

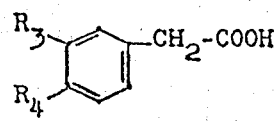

V wherein
$R_3$ and $R_4$ are as defined above,
is converted into an alkyl (1 to 4 carbon atoms) ester thereof, e.g. with an excess of the corresponding alkanol in the presence of an acid, e.g. hydrochloric acid. The resulting ester is reacted in the presence of a strongly basic condensation agent, such as sodium ethylate in toluene, with a dialkyl (alkyl of 1 to 4 carbon atoms) ester of oxalic acid. The resulting compound of formula VI,

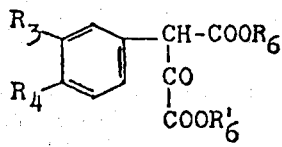

VI wherein
$R_3$ and $R_4$ are as defined above, and each of
$R_6$ and $R'_6$ is alkyl of 1 to 4 carbon atoms,
is treated with formaldehyde, e.g. with aqueous formalin, in the presence of an alkali such as potassium carbonate, and the reaction product is distilled, whereby a phenylacrylic acid ester of formula VII,

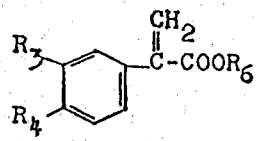

VII wherein
$R_3$, $R_4$ and $R_6$ are as defined above, is obtained.

The phenylacrylic acid ester of formula VII is condensed with methylamine and the condensation product is reacted with a compound of formula VIII,

VIII wherein
Y is chlorine or bromine, and
$R_7$ is alkyl of 1 to 4 carbon atoms,
in the presence of an acid-binding agent, whereby a compound of formula IX,

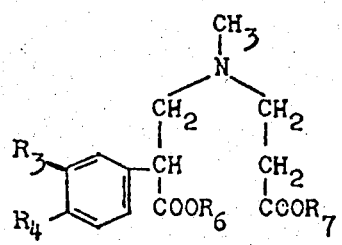

IX wherein
$R_3$, $R_4$, $R_6$ and $R_7$ are as defined above, is obtained. However, a compound of formula IX may also be obtained by reacting a phenylacrylic acid ester of formula VII with an amino acid ester of formula X,

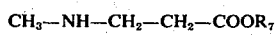

X wherein
$R_7$ is as defined above.

The compound of formula IX is cyclized by heating with a strongly basic condensation agent, e.g. sodium hydride in toluene, and the resulting product is converted into the corresponding piperidone of formula XI,

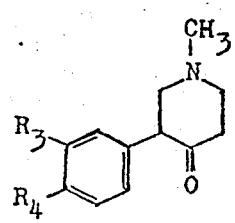

XI wherein
$R_3$ and $R_4$ are as defined above,
by hydrolysis and decarboxylation, e.g. by heating in an aqueous mineral acid such as 3-6 N hydrochloric acid.

The piperidones of formula XI are reacted with hydroxylamine hydrochloride and the resulting oximes are reduced to the corresponding piperidyl amines, e.g. by hydrogenation over a metal catalyst such as Raney nickel, by reaction with complex alkali metal hydrides such as lithium aluminum hydride, or with metallic sodium in a lower alkanol. The piperidones of formula XI may also be hydrogenated catalytically in the presence of ammonia, e.g. in a solution of ammonia in ethanol in the presence of Raney nickel at an elevated temperature and under pressure, whereby the imines resulting as intermediaries are reduced in situ to the corresponding piperidylamines. The reductions mentioned above generally yield mixtures of the cis- and transracemates, the percentage composition of which will vary depending on the reaction conditions. The cis-piperidylamines of formula III may be separated from these mixtures as racemates in accordance with known methods, e.g. by fractional crystallization of their acid addition salts or by adsorption chromatography.

Insofar as the production of the starting materials is not described, these are known or may be produced in accordance with known processes or in a manner analogous to the processes described herein or to known processes.

The compounds of formula I and their pharmacologically tolerable acid addition salts are useful because they possess pharmacological activity in animals. More particularly, the compounds are useful in the treatment of thrombosis as indicated by their properties in inhibiting blood platelet aggregation, this property being illustrated by the inhibition of such aggregation caused in vitro by adenosine diphosphate in blood platelet-rich rabbit plasma (turbidimetric method in accordance with Born), and by inhibition of thrombosis in the aortic loop rat preparation. Inhibition commences at concentrations from about 1 µg/ml to about 30 µg/ml in the in vitro test.

For the above-mentioned use, the dose will naturally vary depending on the compound employed, the mode of administration and the treatment desired. However, satisfactory results are obtained in warm-blooded animals at a dose of from about 0.1 to about 10 mg/kg animal body weight, conveniently given in divided doses 2 to 3 times a day, or in sustained release form. For the larger mammals, the daily dosage is from about 10 mg to about 400 mg, and dosage forms suitable for oral administration contain from about 3 to about 200 mg of the compound admixed with the solid or liquid pharmaceutical carrier or diluent.

The compounds of formula I may be administered in pharmaceutically acceptable acid addition salt form. Such salts possess the same order of activity as the free bases and are readily prepared in conventional manner. Suitable such salt forms include mineral acid salts, such as the hydrochloride, hydrobromide and sulphate, and organic acid salts, succh as the fumarate, maleate, tartrate, methane-, ethane- and benzene-sulphonate, citrate and malate.

The invention also provides a pharmaceutical composition comprising as active agent a compound of formula I, or a pharmaceutically acceptable acid addition salt thereof, in association with a pharmaceutically acceptable carrier or diluent.

In the following illustrative Examples all temperatures are indicated in degrees Centigrade and are uncorrected.

EXAMPLE 1:

cis-1,2,3,4,4a,10b-Hexahydro-8,9-dimethoxy-2-methyl-6-phenyl-benzo[c][1,6]naphthyridine.

a. 15 g of cis-4-amino-3-(3,4-dimethoxyphenyl)-1-methylpiperidine are dissolved in 30 cc of dioxane and 33 cc of a 2 N caustic soda solution, and a solution of 9 cc of benzoyl chloride in 30 cc of dioxane is added dropwise within 20 minutes at room temperature while stirring. The resulting white crystalline mash is rendered strongly alkaline with a 2 N caustic soda solution, is diluted with water and filtered off. After recrystallization from ethyl acetate cis-4-benzoylamino-3-(3,4-dimethoxyphenyl)-1-methylpiperidine is obtained as white fine crystals having a M.P. of 134°–135°.

b. 18 g of cis-4-benzoylamino-3-(3,4-dimethoxyphenyl)-1-methylpiperidine are boiled under reflux in 100 cc of phosphorus oxychloride for 1½ hours. The reaction mixture is subsequently evaporated to dryness in a vacuum and the resulting oily residue is shaken with methylene chloride and a 2 N caustic soda solution. The organic phase is dried over sodium sulphate and concentrated by evaporation. Crystallization from ethyl acetate yields the title compound as almost colourless crystals having a M.P. of 126°–127°.

In a manner analogous to Example 1 above, employing the corresponding starting materials, the following compounds are obtained:

cis-6-(2-Fluorphenyl)-8,9-dimethoxy-2-methyl-1,2,3,4,4a,10b-hexahydro-benzo[c][1,6]naphthyridine (M.P. of dihydrochloride 238°–240°)

cis-6-(4-Aethoxyphenyl)-8,9-dimethoxy-2-methyl-1,2,3,4,4a,10b-hexahydro-benzo[c][1,6]naphthyridine (M.P. of dihydrochloride 250°–252°)

cis-8,9-Dimethoxy-2-methyl-6-(2,3-dimethylphenyl)-1,2,3,4,4a,10b-hexahydro-benzo[c][1,6]naphthyridine (M.P. of dihydrochloride 250°–252°)

cis-8,9-Dimethoxy-2-methyl-6-(3,5-dimethylphenyl)-1,2,3,4,4a,10b-hexahydro-benzo[c][1,6]naphthyridine (M.P. of dihydrochloride 218°–222°)

cis-8,9-Dimethoxy-2-methyl-6-(2,4-dimethylphenyl)-1,2,3,4,4a,10b-hexahydro-benzo[c][1,6]naphthyridine (M.P. of dihydrochloride 238°–240°)

cis-8,9-Dimethoxy-6-(2,3-dimethoxyphenyl)-2-methyl-1,2,3,4,4a,10b-hexahydro-benzo[c][1,6]naphthyridine (M.P. of dihydrochloride 195°–200°)

cis-8,9-Dimethoxy-6-(3,5-dimethoxyphenyl)-2-methyl-1,2,3,4,4a,10b-hexahydro-benzo[c][1,6]naphthyridine (M.P of dihydrochloride 219°–222°)

cis-8,9-Dimethoxy-2-methyl-6-(3-methyl-4-nitrophenyl)-1,2,3,4,4a,10b-hexahydro-benzo[c][1,6]naphthyridine (M.P. of dihydrochoride 236°–238°)

cis-6-(4-Chloro-3-nitrophenyl)-8,9-dimethoxy-2-methyl-1,2,3,4,4a,10b-hexahydro-benzo[c][1,6]naphthyridine (M.P. of dihydrochloride 220°–225°).

cis-8,9-Dimethoxy-2-methyl-6-(4-methyl-3-nitrophenyl)-1,2,3,4,4a,10b-hexahydro-benzo[c][1,6]naphthyridine (M.P. of dihydrochloride 218°–222°)

EXAMPLE 2:

cis-6-(3,4-Dichlorophenyl)-1,2,3,4,4a,10b-hexahydro-8,9-dimethoxy-2-methyl-benzo[c][1,6]naphthyridine.

cis-4-(3,4-Dichlorobenzoylamino)-3-(3,4-dimethoxyphenyl)-1-methylpiperidine [M.P. 134°–135°, obtained in analogy to Example 1 a)] is cyclized in analogy to the process described in Example 1 b). The title compound has a M.P. of 183°–184° (from ethyl acetate).

EXAMPLE 3:

cis-1,2,3,4,4a,10b-Hexahydro-8,9-dimethoxy-6-(3,4-dimethoxyphenyl)-2-methyl-benzo[c][1,6]naphthyridine.

a. 9.7 g of cis-4-amino-3-(3,4-dimethoxyphenyl)-1-methylpiperidine dihydrochloride are allowed to stand together with 8.3 g of 3,4-dimethoxybenzoyl chloride in 50 cc of dry pyridine at room temperature for 20 hours. 20 cc of water are subsequently added to the reaction mixture while cooling, and this is allowed to stand at room temperature for a further 30 minutes. The reaction mixture is then diluted with 400 cc of water and 50 cc of a 2 N caustic soda solution, extraction is effected with methylene chloride, the organic phase being dried over sodium sulphate and concentrated by evaporation in a vacuum. The cis-4-(3,4-dimethoxybenzoylamino)-3-(3,4-dimethoxyphenyl)-1-methylpiperidine is used for the next reaction without further purification.

b. cis-4-(3,4-Dimethoxybenzoylamino)-3-(3,4-dimethoxyphenyl)-1-methylpiperidine is cyclized in accordance with the process described in Example 1 b). The title compound has a M.P. of 199°–201° (from ethyl acetate).

EXAMPLE 4:

cis-1,2,3,4,4a,10b-Hexahydro-8,9-dimethoxy-2-methyl-6-(4-nitrophenyl)-benzo[c][1,6]naphthyridine.

a. 7.45 g of cis-4-amino-3-(3,4-dimethoxyphenyl)-1-methylpiperidine and 5.55 g of 4-nitrobenzoyl chloride in 50 cc of pyridine are heated to 60° for 3 hours. The reaction mixture is cooled, is rendered strongly alkaline with concentrated caustic soda solution and is gradually diluted with a total of 200 cc of water, whereby the product is obtained in crystalline form and may be filtered off. After crystallization from ethyl acetate the cis-3-(3,4-dimethoxyphenyl)-1-methyl-4-(4-nitrobenzoylamino)-piperidine has a M.P. of 167°.

b. cis-3-(3,4-Dimethoxyphenyl)-1-methyl-4-(4-nitrobenzoylamino)-piperidine is cyclized in analogy to the process described in Example 1 b). The title compound has a M.P. of 194°–195° (from ethyl acetate).

EXAMPLE 5:

cis-6-(4-Aminophenyl)-1,2,3,4,4a,10b-hexahydro-8,9-dimethoxy-2-methyl-benzo[c][1,6]naphthyridine.

2,7 g of iron turnings are added to a hot solution of 2.0 g of cis-1,2,3,4,4a,10b-hexahydro-8,9-dimethoxy-2-methyl-6-(4-nitrophenyl)-benzo[c][1,6]naphthyridine in 40 cc of ethanol and 13 cc of water. A mixture of 13 cc of ethanol, 3 cc of water and 0.7 cc of 2 N hydrochloric acid is added dropwise within 40 minutes while heating, and the reaction mixture is boiled under reflux for a further 3 hours. 1 cc of a 2 N caustic soda solution is then added, filtration is effected and the filtrate is concentrated by evaporation in a vacuum. The residue is dissolved in chloroform, the solution is dried over sodium sulphate, filtered and concentrated by evaporation in a vacuum. The residue is crystallized from ethyl acetate, whereby yellowish prisms having a M.P. of 168°–170°, are obtained.

In a manner analogous to Example 5 above, employing the corresponding starting materials, the following compounds are obtained:

cis-6-(3-Aminophenyl)-8,9-dimethoxy-2-methyl-1,2,3,4,4a,10b-hexahydro-benzo[c][1,6]naphthyridine (M.P. of trihydrochloride 268°–270°)

cis-6-(2-Aminophenyl)-8,9-dimethoxy-2-methyl-1,2,3,4,4a,10b-hexahydro-benzo[c][1,6]naphthyridine (M.P. 174°–175°)

EXAMPLE 6:

cis-6-(4-Acetamidophenyl)-1,2,3,4,4a,10b-hexahydro-8,9-dimethoxy-2-methyl-benzo[c][1,6]naphthyridine.

1.0 g of cis-6-(4-aminophenyl)-1,2,3,4,4a,10b-hexahydro-8,9-dimethoxy-2-methyl-benzo[c][1,6]naphthyridine (produced as in Example 5) is heated to 60° in a mixture of 2 cc of pyridine and 2 cc of acetic anhydride for 2 hours. The reaction mixture is then evaporated to dryness in a vacuum and the residue is crystallized from acetone. M.P. 173°–175°.

EXAMPLE 7:

cis-8,9-Dimethoxy-2-methyl-6-(4-pivaloylaminophenyl)-1,2,3,4,4a,10b-hexahydro-benzo[c][1,6]naphthyridine 2 g of 6-(4-aminophenyl)-8,9-dimethoxy-2-methyl-1,2,3,4,4a,10b-hexahydro-benzo[c][1,6]naphthyridine, 10 ml of pyridine and 6 ml of pivalic acid anhydride are heated at 60° for 2 hours. The reaction mixture is then treated with 10 ml of water and evaporated to dryness under vacuum. The resulting oily residue is dissolved in ethanol and treated with a small excess of ethanolic hydrochloric acid, whereby the dihydrochloride of the title compound crystallizes out in yellowish prisms of M.P. 245°.

EXAMPLE 8:

cis-6-(4-Benzoylaminophenyl)-8,9-dimethoxy-2-methyl-1,2,3,4,4a,10b-hexahydro-benzo[c][1,6]naphthyridine 2 g of 6-(4-aminophenyl)-8,9-dimethoxy-2-methyl-1,2,3,4,4a,10b-hexahydro-benzo[c][1,6]naphthyridine are dissolved in 30 ml of pyridine, 1 g of benzoylchloride is added to the solution and the reaction mixture is allowed to stand at room temperature for 15 hours. The reaction mixture is then treated with 10 ml of water, allowed to stand for 10 minutes and is then reduced in volume under vacuum. The resulting residue is rendered alkaline with dilute sodium hydroxide and is then extracted with methylenechloride. After evapaorating off of the organic phase, the crude product is dissolved in ethanol and rendered acid with an ethanolic hydrochloric acid solution, whereby the dihydrochloride of the title compound crystallizes out in yellowish prisms of M.P. 240°–245°.

EXAMPLE 9:

cis-6-(3-Benzoylaminophenyl)-8,9-dimethoxy-2-methyl-1,2,3,4,4a,10b-hexahydro-benzo[c][1,6]naphthyridine 2 g of
cis-6-(3-aminophenyl)-8,9-dimethoxy-2-methyl-1,2,3,4,4a,10b-hexahydro-benzo[c][1,6]naphthyridine are dissolved in 30 ml of pyridine, 1 g of benzoylchloride is added and the reaction mixture is allowed to stand for 15 hours at room temperature. The reaction mixture is treated with 10 ml of water, allowed to stand for 10 minutes and is then reduced in volume under vacuum. The resulting residue is rendered alkaline with diluted sodium hydroxide and is then extracted with methylenechloride. After evaporating off of the organic phase, the crude product is dissolved in ethanol and rendered acid with an ethanolic hydrochloric acid solution, whereby the dihydrochloride of the title compound crystallizes out in yellow crystals of M.P 247°–250°.

In a manner analogous to Example 6 to 9 above, acylation is effected by reaction of a cis-6-(aminophenyl)-1,2,3,4,4a,10b-hexahydro-8,9-dimethoxy-2-methyl-benzo[c][1,6]naphthyridine, or a cis-6-(aminophenyl)-1,2,3,4,4a,10b-hexahydro-8,9-methylenedioxy-2-methylbenzo[c][1,6]naphthyridine, or a cis-6-(aminophenyl)-1,2,3,4,4a,10b-hexahydro-2-methyl-benzo[c][1,6]naphthyridine, with the chloride or anhydride of acetic acid, propionic acid, stearic acid, phenacetic. acid, 2,4-dimethyl-phenacetic acid, 3,5-dimethoxy-phenacetic acid, 2-fluoro or 2-chloro or 2-bromo benzoic acid, cinnamic acid, nicotinic acid, 3-thiophene carboxylic acid, 3-furan carboxylic acid, or with 2-pyrrole carboxylic acid anhydride, to obtain the corresponding 2-, 3- or 4- acylamino naphthyridine. Examples of compounds obtained are:

cis-6-(3-Acetanilido)-8,9-dimethoxy-2-methyl-1,2,3,4,4a,10b-hexahydro-benzo[c][1,6]naphthyridine (M.P. of dihydrochloride 268°–270°)

cis-8,9-Dimethoxy-2-methyl-6-(4-propionylaminophenyl)-1,2,3,4,4a,10b-hexahydro-benzo[c][1,6-]naphthyridine (M.P. of bis-hydrogenfumarate 216°–218°), and 2-, 3- or 4-acylamino naphthyridines, wherein the acyl group is selected from stearyl, phenacetyl, 2,4-dimethylphenacetyl, 3,5-dimethoxy-phenacetyl, 2-fluoro- or 2-chloro or 2-bromo-benzoyl, cinnamoyl, nicotinoyl, 3-thenoyl, 3-furoyl and 2-pyrroyl.

EXAMPLE 10:

cis-1,2,3,4,4a,10b-Hexahydro-6-(3,5-dimethoxyphenyl)-2-methyl-benzo[c][1,6]naphthyridine.

cis-4-(3,5-Dimethoxybenzoylamino)-1-methyl-3-phenylpiperidine [M.P. 123°–124°, obtained in analogy to Example 12 a) hereinafter] is cyclized in analogy to the process described in Example 1 b). The title compound has a M.P. of 123°–124° (from ethyl acetate).

EXAMPLE 11:

cis-1,2,3,4,4a,10b-Hexahydro-8,9-dimethoxy-2-methyl-6-(p-tolyl)-benzo[c][1,6]naphthyridine.

7.35 g of cis-3-(3,4-dimethoxyphenyl)-1-methyl-4-(4-toluoylamino)-piperidine [M.P. 145°–146°, obtained in analogy to Example 1 a)] and 35 cc of phosphorus oxychloride are reacted as described in Example 1 b). The residue obtained after evaporation of the solvent is dissolved in 200 cc of acetone. After the addition of 8.5 cc of a 5 N solution of hydrochloric acid in ethanol, the dihydrochloride of the title compound is obtained. M.P. 257°.

EXAMPLE 12:

cis-1,2,3,4,4a,10b-Hexahydro-8,9-dimethoxy-6-(4-methoxyphenyl)-2-methyl-benzo[c][1,6]naphthyridine.

cis-4-(4-Methoxybenzoylamino)-3-(3,4-dimethoxyphenyl)-1-methylpiperidine [M.P. 223°–226°, obtained in analogy to Example 1 a)] is cyclized in analogy to the process described in Example 8. The dihydrochloride of the title compound has a M.P. of 250°–252° (from ethanol).

EXAMPLE 13:

cis-6-(4-Chlorophenyl)-1,2,3,4,4a,10b-hexahydro-8,9-dimethoxy-2-methyl-benzo[c][1,6]naphthyridine.

cis-4(4-Chlorobenzoylamino)-3-(3,4-dimethoxyphenyl)-1-methylpiperidine [crude product, obtained in analogy to Example 1 a)] is cyclized in analogy to the process described in Example 8. The dihydrochloride of the title compound has a M.P. of 245° (from ethanol).

EXAMPLE 14:

cis-6-(2-Chlorophenyl)-1,2,3,4,4a,10b-hexahydro-8,9-dimethoxy-2-methyl-benzo[c][1,6]naphthyridine.

cis-4-(2-Chlorobenzoylamino)-3-(3,4-dimethoxyphenyl)-1-methylpiperidine [crude product, obtained in analogy to Example 1 a)] is cyclized in analogy to the process described in Example 8. The dihydrochloride of the title compound has a M.P. of 223°–226° (from ethanol).

EXAMPLE 15:

cis-6-(4-Fluorophenyl)-1,2,3,4,4a,10b-hexahydro-8,9-dimethoxy-2-methyl-benzo[c][1,6]naphthyridine.

a. A solution of 6 g of cis-4-amino-3-(3,4-dimethoxyphenyl)-1-methylpiperidine and 4.6 g of 4-fluorobenzoyl chloride in 50 cc of pyridine is heated at 60° for 3 hours. The reaction mixture is strongly concentrated under vacuum, water is added, and the mixture is allowed to stand at room temperature for 1 hour. The reaction mixture is rendered strongly alkaline with dilute potassium carbonate solution and the aqueous phase is extracted thrice with chloroform. The organic phases are combined, dried overe sodium sulphate and concentrated by evaporation in a vacuum. The residue is crystallized from ethyl acetate/pentane (1:1 by volume), whereby the pure cis-4-(4-fluorobenzoylamino)-3-(3,4-dimethoxyphenyl)-1-methylpiperidine is obtained as yellowish prisms having a M.P. of 130°–132°.

b. cis-4-(4-Fluorobenzoylamino)-3-(3,4-dimethoxyphenyl)-1-methylpiperidine is cyclized in analogy to the process described in Example 8. The dihydrochloride of the title compound has a M.P. of 250°–255° (from ethanol).

EXAMPLE 16:

cis-1,2,3,4,4a,10b-Hexahydro-8,9-dimethoxy-2-methyl-6-(4-methylthiophenyl)-benzo[c][1,6]naphthyridine.

cis-3-(3,4-Dimethoxyphenyl)-1-methyl-4-(4-methylthiobenzoylamino)-piperidine [M.P. 144°–146°, obtained in analogy to Example 4 a)] is cyclized in analogy to the process described in Example 8. The dihydrochloride of the title compound has a M.P. of 227°–230° (from ethanol/acetone).

EXAMPLE 17:

cis-1,2,3,4,4a,10b-Hexahydro-8,9-dimethoxy-2-methyl-6-(4-nitrophenyl)-benzo[c][1,6]naphthyridine.

cis-3-(3,4-Dimethoxypheny)-1-methyl-4-(4-nitrobenzoylamino)-piperidine [M.P. 167°, see Example 4 a)] is cyclized in analogy to the process described in Example 8. The dihydrochloride of the title compound has a M.P. of 225°–230° (from ethanol).

EXAMPLE 18:

cis-1,2,3,4,4a,10b-Hexahydro-2-methyl-6-phenylbenzo[c][1,6]naphthyridine.

cis-4-Benzoylamino-1-methyl-3-phenylpiperidine [M.P. 154°–155°, obtained in analogy to Example 4 a)] is cyclized in analogy to the process described in Example 8. The dihydrochloride of the title compound has a M.P. of 243°–244° (from ethanol).

EXAMPLE 19:

cis-1,2,3,4,4a,10b-Hexahydro-6-(4-methoxyphenyl)-2-methyl-benzo[c][1,6]naphthyridine.

cis-4-(4-Methoxybenzoylamino)-1-methyl-3-phenylpiperidine [M.P. 165°–166°, obtained in analogy to Example 12 a)] is cyclized in analogy to the process described in Example 8. The dihydrochloride of the title compound has a M.P. of 269°–270° (from ethanol).

EXAMPLE 20:

cis-1,2,3,4,4a,10b-Hexahydro-6-(3,4-dimethoxyphenyl)-2-methyl-benzo[c][1,6]naphthyridine.

cis-4(3,4-Dimethoxybenzoylamino)-1-methyl-3-phenylpiperidine [M.P. 153°–155°, obtained in analogy to Example 12 a)] is cyclized in analogy to the process described in Example 8. The dihydrochloride of the title compound has a M.P. of 220°–222° (from ethanol).

EXAMPLE 21:

cis-6-(3-Trifluoromethylphenyl)-1,2,3,4,4a,10b-hexahydro-8,9-dimethoxy-2-methyl-benzo[c][1,6]naphthyridine.

cis-4-(3-Trifluoromethyl-benzoylamino)-3-(3,4-dimethoxyphenyl)-1-methylpiperidine [M.P. 122°–124°, obtained in analogy to Example 12 a)] is cyclized in analogy to the process described in Example 8. The dihydrochloride of the title compound has a M.P. of 215°–217° (from ethanol).

EXAMPLE 22:

cis-1,2,3,4,4a,10b-Hexahydro-2-methyl-8,9-methylenedioxy-6-phenyl-benzo[c][1,6]naphthyridine.

a. 5.0 g of cis-4-amino-3-(3,4-methylenedioxyphenyl)-1-methylpiperidine are dissolved in 50 cc of chloroform, and a solution of 3.3. g of benzoyl chloride in 10 cc of chloroform is added at 0°. The reaction solution is allowed to stand at room temperature for 2 hours and is extracted with a saturated potassium carbonate solution and subsequently with water. The chloroform layer is dried over sodium sulphate and concentrated by evaporation. The residue is recrystallized from acetone. The cis-4-benzoylamino-3-(3,4-methylenedioxyphenyl)-1-methylpiperidine has a M.P. of 175°–177°.

b. 7.0 g of cis-4-benzoylamino-3-(3,4-methylenedioxyphenyl)-1-methylpiperidine are heated to 90° in 75 cc of phosphorus oxychloride for 20 hours. The reaction mixture is subsequently evaporated to dryness, the residue is dissolved in 50 cc of ice water and a saturated potassium carbonate solution is added until the mixture is strongly alkaline. The reaction mixture is extracted with chloroform, and the chloroform mixture is washed with water, dried over sodium sulphate, and the solvent is evaporated. The residue is taken up in 20 cc of ethanol, and absolute hydrochloric acid in ethanol is added until an acid reaction to Congo red is obtained and precipitation is effected with ether. The precipitate, the dihydrochloride of the title compound, is recrystallized from ethanol/ether. Yellow coloured crystals having a M.P. of 248° (decomp.).

EXAMPLE 23:

cis-1,2,3,4,4a,10b-Hexahydro-6-(3,4-dimethoxyphenyl)-2-methyl-8,9-methylenedioxy-benzo[c][1,6]naphthyridine.

8.0 g of crude cis-4-(3,4-dimethoxybenzoylamino)-3-(3,4-methylenedioxyphenyl)-1-methylpiperidine [crude product, obtained in analogy to Example 19 a)] are heated to 90° in 75 cc of phosphorous oxychloride for 18 hours. The phosphorus oxychloride is subsequently distilled off and the resulting residue is taken up in water. The reaction solution is rendered alkaline with an excess of a saturated potassium carbonate solution and extraction is effected with chloroform. The chloroform layer is washed with water, dried over sodium sulphate and concentrated by evaporation. The dark residue is dissolved in ethanol and an excess of maleic acid is added. The yellow coloured bis-hydrogen maleate of the title compound crystallizes upon cooling and has a M.P. of 193°–194° after recrystallization from methanol.

EXAMPLE 24 cis-8,9-Dimethoxy-2-methyl-6-(3,4-dimethylphenyl)-1,2,3,4,4a,10b-hexahydro-benzo[c][1,6]naphthyridine.

cis-3-(3,4-Dimethoxyphenyl)-1-methyl-4-(3,4-dimethylbenzoylamino)-piperidine is cyclized in analogy to the process described in Example 1 b). The bis-hydrogen maleate of the title compound has a M.P. of 182°–184° (from ethanol).

EXAMPLE 25:

Cis-6-(4-formamidophenyl)-8,9-dimethoxy-2-methyl-1,2,3,4,4a,10b-hexahydro-benzo[c][1,6]naphthyridine 2,1 g of cis-6-(4-aminophenyl)-8,9-dimethoxy-2-methyl-1,2,3,4,4a,10b-hexahydro-benzo[c][1,6] naphthyridine are heated to 100° for 2½ hours in 50 ml of 90% formic acid. The reaction solution is evaporated to dryness in a vacuum, the resulting residue is made alkaline with a dilute potash solution and this aqueous phase is extracted with methylene chloride. After drying and concentrating the organic phase by evaporation, the title compound is obtained as a yellow oil and crystallizes after the addition of ethanol in the form of yellowish prisms having a melting point of 140°–145°.

EXAMPLE 26:

Cis-6-(3-formamidophenyl)-8,9-dimethoxy-2-methyl-1,2,3,4,4a,10b-hexahydro-benzo[c][1,6]naphthyridine 2,6 g of cis-6-(3-aminophenyl)-8,9-dimethoxy-2-methyl-1,2,3,4,4a,10b-hexahydro-benzo[c][1,6]naphthyridine are heated to 100° for 2½ hours in 50 ml of 90% formic acid. The reaction solution is evaporated to dryness in a vacuum, the resulting residue is made alkaline with a dilute potash solution and this aqueous phase is extracted with methylene chloride. After drying and concentrating the organic phase by evaporation, the title compound is obtained as yellowish foam and crystallizes after the addition of acetone in the form of yellowish prisms having a melting point of 209°–210°.

EXAMPLE 27:

Cis-6-(4-caproylamidophenyl)-8,9-dimethoxy-2-methyl-1,2,3,4,4a,10b-hexahydro-benzo[c][1,6]naphthyridine The title compound is obtained in a manner analogous to that described in Example 7 by acylation of 6-(4-aminophenyl)-8,9-dimethoxy-2-methyl-1,2,3,4,4a,10b-hexahydro-benzo[c][1,6]naphthyridine with caproyl chloride in pyridine.

(Melting point of the dihydrochloride form: 235°–238°, crystallization from ethanol).

EXAMPLE 28:

Cis-6-(4-lauroylamidophenyl)-8,9-dimethoxy-2-methyl-1,2,3,4,4a,10b-hexahydro-benzo[c][1,6]naphthyridine

The title compound is obtained in a manner analogous to that described in Example 7 by acylation of 6-(4-aminophenyl)-8,9-dimethoxy-2-methyl-1,2,3,4,4a,10b-hexahydro-benzo[c][1,6]naphthyridine with lauroyl chloride in pyridine.

(Melting point of the dihydrochloride form: 210°–215°, crystallization from aethanol).

EXAMPLE 29:

Cis-8,9-dimethoxy-2-methyl-6-(4-stearoylamidophenyl)-1,2,3,4,4a,10b-hexahydro-benzo[c][1,6-]naphthyridine.

The title compound is obtained in a manner analogous to that described in Example 7 by acylation of 6-(4-aminophenyl)-8,9-dimethoxy-2-methyl-1,2,3,4,4a,10b-hexahydro-benzo[c][1,6]naphthyridine with stearoyl chloride in pyridine.

(Melting point of the dihydrochloride form: 215°–220°, crystallization from ethanol).

EXAMPLE 30:

Cis-8,9-dimethoxy-2-methyl-6-(4-nonanoylaminophenyl)-1,2,3,4,4a,10b-hexahydro-benzo[c][1,6-]naphthyridine The title compound is obtained in a manner analogous to that described in Example 7 by acylation of 6-(4-aminophenyl)-8,9-dimethoxy-2-methyl-1,2,3,4,4a,10b-hexahydro-benzo[c][1,6]naphthyridine with nonanoyl chloride. (Melting point of dihydrochloride form: 220°–225°, crystallization from ethanol).

EXAMPLE 31:

Cis-8,9-dimethoxy-2-methyl-6-(4-pentanoylaminophenyl)-1,2,3,4,4a,10b-hexahydrobenzo[c][1,6]naphthyridine 3 g of 6-(4-aminophenyl)-8,9-dimethoxy-2-methyl-1,2,3,4,4a,10b-hexahydro-benzo[c][1,6]naphthyridine and 6,2 g of valeric acid chloride are heated to the boil under reflux in 70 ml of acetonitrile for 7 hours. The reaction mixture is evaporated to dryness in a vacuum, water is added to the residue, the reaction mixture is made alkaline with potassium carbonate and extracted with methylene chloride. The solution is concentrated by evaporation, the crude product is dissolved in ethanol and a slight excess of hydrochloric acid in ethanol is added, whereby the title compound crystallizes in dihydrochloride form (melting point: 230°–235°).

EXAMPLE 32:

Cis-6-(4-isobutyroylaminophenyl)-8,9-dimethoxy-2-methyl-1,2,3,4,4a,10b-hexahydro-benzo[c][1,6]naphthyridine The title compound is obtained in a manner analogous to that described in Example 7 by acylation of 6-(4-aminophenyl)-8,9-dimethoxy-2-methyl-1,2,3,4,4a,10b-hexahydro-benzo[c][1,6]naphthyridine with isobutyroyl chloride. (Melting point of the dihydrochloride form: 233°–238°, from ethanol).

EXAMPLE 33:

Cis-6-[4-(2-furoylamino)phenyl]-8,9-dimethoxy-2-methyl-1,2,3,4,4a,10b-hexahydro-benzo[c][1,6]naphthyridine The title compound is obtained in a manner analogous to that described in Example 7 by acylation of 6-(4-aminophenyl)-8,9-dimethoxy-2-methyl-1,2,3,4,4a,10b-hexahydro-benzo[c][1,6]naphthyridine with 2-furan-carboxylic acid chloride in pyridine (over night at room temperature). After working up and purifying in a manner analogous to that described in Example 31, the dihydrochloride form of the title compound, having a melting point of 251°–255°, is obtained.

EXAMPLE 34:

Cis-8,9-dimethoxy-2-methyl-4-[4-(2-thenoylamino)-phenyl]-1,2,3,4,4a,10b-hexahydro-benzo[c][1,6-]naphthyridine The title compound is obtained in a manner analogous to that described in Example 33 by acylation of 6-(4-aminophenyl)-8,9-dimethoxy-2-methyl-1,2,3,4,4a,10b-hexahydro-benzo[c][1,6]naphthyridine with 2-thiophene carboxylic acid chloride. Melting point of the dihydrochloride form; 246°–249°.

EXAMPLE 35:

Cis-8,9-dimethoxy-2-methyl-6-(4-nicotinoyl-aminophenyl)-1,2,3,4,4a,10b-hexahydro-benzo[c][1,6-]naphthyridine The title compound is obtained in a manner analogous to that described in Example 33 by acylation of 6-(4-aminophenyl)-8,9-dimethoxy-2-methyl-1,2,3,4,4a,10b-hexahydro-benzo[c][1,6]naphthyridine with nicotinic acid chloride. (Melting point of the trihydrochloride form: 248°–251°).

EXAMPLE 36:

Cis-6-[4-(4-chlorobenzamido)phenyl]-8,9-dimethyoxy-2-methyl-1,2,3,4,4a,10b-hexahydro-benzo[c][1,6]naphthyridine 3,5 g of 6-(4-aminophenyl)-8,9-dimethoxy-2-methyl-1,2,3,4,4a,10b-hexahydro-benzo[c][1,6]naphthyridine are dissolved in 40 ml of pyridine and after the addition of 2,7 g of p-chlorobenzoyl chloride the solution is allowed to stand at room temperature over night. After working up and purifying in a manner analogous to that described in Example 31, the dihydrochloride form of the title compound (melting point 236°–240°) is obtained.

EXAMPLE 37:

Cis-8,9-dimethoxy-2-methyl-6-(4-phenylacetamidophenyl)-1,2,3,4,4a,10b-hexahydro-benzo[c][1,6-]naphthyridine 30g of 6-(4-aminophenyl)-8,9-dimethoxy-2-methyl-1,2,3,4,4a,10b-hexahydro-benzo[c][1,6]naphthyridine and 6,0 g of phenylacetic acid chloride are heated to the boil under reflux in 70 ml of acetonitrile for 7 hours. After working up in a manner analogous to that described in Example 31, and upon adding dilute hydrochloric acid in ethanol to the crude product, the dihydrochloride form of the title compound slowly crystallizes (melting point 240°–245°).

EXAMPLE 38:

Cis-6-(4-cinnamoylaminophenyl)-8,9-dimethoxy-2-methyl-1,2,3,4,4a,10b-hexahydro-benzo[c][1,6]naphthyridine The title compound is obtained in a manner analogous to that described in Example 37 by acylation of 6-(4-aminophenyl)-8,9-dimethoxy-2-methyl-1,2,3,4,4a,10b-hexahydro-benzo[c][1,6]naphthyridine with cinnamoyl chloride. (Melting point of the dihydrochloride form: 242°-246°).

The following compounds are produced using the process described in Example 36 and the appropriate starting materials:

Cis-6-[4-(3-methyl-4-methoxybenzamido)phenyl]-8,9-dimethoxy-2-methyl-1,2,3,4,4a,10b-hexahydro-benzo[c][1,6]naphthyridine.

Cis-6-[4(4-bromobenzamido)phenyl]-8,9-dimethoxy-2-methyl-1,2,3,4,4a,10b-hexahydro-benzo[c][1,6]naphthyridine.

Cis-6-[4-(4-fluorobenzamido)phenyl]-8,9-dimethoxy-2-methyl-1,2,3,4,4a,10b-hexahydro-benzo[c][1,6]naphthyridine.

What is claimed is:

1. A method of treating thrombosis in animals, which comprises orally administering to an animal in need of such treatment a therapeutically effective amount of a compound of formula:

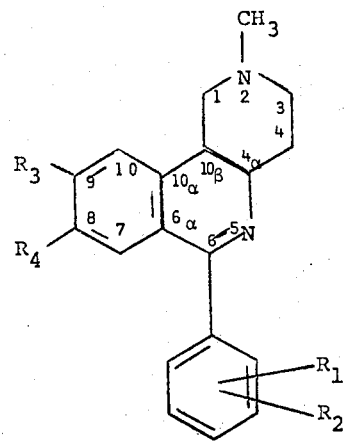

wherein
$R_1$ is hydrogen, alkyl of 1 to 3 carbon atoms, alkoxy of 1 to 3 carbon atoms or alkylthio of 1 to 3 carbon atoms, fluorine, bromine, chlorine, nitro, trifluoromethyl, amino or —NH—CO—R,
wherein
—CO—R is alkanoyl of 1 to 18 carbon atoms, benzoyl, benzoyl wherein the benzene ring is substituted by one X and one Y, X being lower alkyl of 1 to 4 carbon atoms, lower alkoxy of 1 to 4 carbon atoms, fluorine, chlorine, or bromine, and Y being hydrogen, lower alkyl of 1 to 4 carbon atoms, lower alkoxy of 1 to 4 carbon atoms, or chlorine, phenylalkenoyl wherein the akylene section has 1 to 3 carbon atoms, cinnamoyl, phenylalkenoyl as defined above or cinnamoyl which are substituted in the benzene ring by one X and one Y which are as defined above, or A-CO-, A being thienyl, furyl, pyrrolyl, or pyridyl,
$R_2$ is hydrogen, chlorine, alkyl of 1 to 3 carbon atoms or alkoxy of 1 to 3 carbon atoms, and
$R_3$ and $R_4$ are both hydrogen or both methoxy, or
$R_3$ and $R_4$ together are methylenedioxy,
or a pharmaceutically acceptable acid addition salt thereof.

2. The method of claim 1, wherein the compound is of the formula:

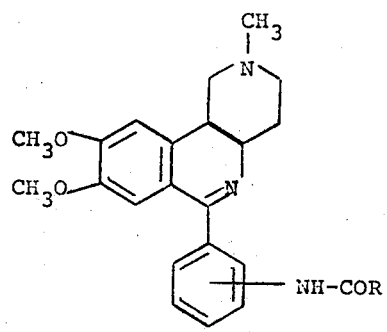

wherein
R is hydrogen, alkyl of 1 to 17 carbon atoms, thienyl, furyl, pyrrolyl, pyridyl or

wherein
A is a direct bond, alkylene of 1 to 3 carbon atoms or vinylene,
X is hydrogen, alkyl of 1 to 4 carbon atoms, alkoxy of 1 to 4 carbon atoms, fluorine, chlorine or bromine, and
Y is hydrogen, alkyl of 1 to 4 carbon atoms or alkoxy of 1 to 4 carbon atoms.

3. The method of claim 1, wherein in the compound $R_1$ is hydrogen, alkyl of 1 to 3 carbon atoms, alkoxy of 1 to 3 carbon atoms or alkylthio of 1 to 3 carbon atoms, fluorine, bromine, chlorine, nitro, trifluoromethyl, amino or amido of 2 to 4 carbon atoms, $R_2$ is hydrogen, chlorine, alkyl of 1 to 3 carbon atoms or alkoxy of 1 to 3 carbon atoms, and $R_3$ and $R_4$ are both hydrogen or methoxy, or $R_3$ and $R_4$ together are methylenedioxy.

4. The method of claim 1, wherein the compound is cis-6-(4-acetamidophenyl)-1,2,3,4,4a,10b-hexyhydro-8,9-dimethoxy-2-methyl-benzo[c][1,6]naphthyridine.

5. The method of claim 1, wherein the compound is cis-1,2,3,4,4a,10b-hexahydro-8,9-dimethoxy-2-methyl-6-phenyl-benzo[c][1,6]naphthyridine.

6. The method of claim 1, wherein the compound is administered at a daily dose of from about 0.1 to about 10 mg/kg animal body weight.

7. The method of claim 6, wherein the compound is administered at a daily dose of from about 10 mg to about 400 mg.

8. The method of claim 7, wherein the compound is orally administered in unit dosage form, containing from about 3 to about 200 mg of the compound.

9. The method of claim 8, wherein the compound is cis-1,2,3,4,4a,10b-hexahydro-8,9-dimethoxy-2-methyl-6-phenyl-benzo[c][1,6]naphthyridine.

10. The method of claim 8, wherein the compound is cis-6-(4-acetamidophenyl)-1,2,3,4,4a,10b-hexahydro-8,9-dimethoxy-2-methyl-benzo[c][1,6]naphthyridine.

11. A method of inhibiting blood platelet aggregation in animals which comprises orally administering to an animal in need of such treatment a therapeutically effective amount of a compound of formula:

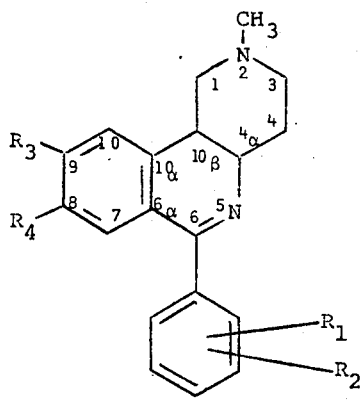

wherein
R₁ is hydrogen, alkyl of 1 to 3 carbon atoms, alkoxy of 1 to 3 carbon atoms or alkylthio of 1 to 3 carbon atoms, fluorine, bromine, chlorine, nitro, trifluoromethyl, amino or —NH—CO—R, wherein
—CO—R is alkanoyl of 1 to 18 carbon atoms, benzoyl, benzoyl wherein the benzene ring is substituted by one X and one Y, X being lower alkyl of 1 to 4 carbon atoms, lower alkoxy of 1 to 4 carbon atoms, fluorine, chlorine, or bromine, and Y being hydrogen, lower alkyl of 1 to 4 carbon atoms, lower alkoxy of 1 to 4 carbon atoms, or chlorine, phenylalkenoyl, wherein the alkylene section has 1 to 3 carbon atoms, cinnamoyl, phenylalkenoyl as defined above or cinnamoyl which are substituted in the benzene ring by one X and one Y which are as defined above, or A-CO-, A being thienyl, furyl, pyrrolyl, or pyridyl,
R₂ is hydrogen, chlorine, alkyl of 1 to 3 carbon atoms, or alkoxy of 1 to 3 carbon atoms, and
R₃ and R₄ are both hydrogen or both methoxy, or
R₃ and R₄ together are methylenedioxy,
or a pharmaceutically acceptable acid addition salt thereof.

12. The method of claim 11, wherein the compound is of the formula:

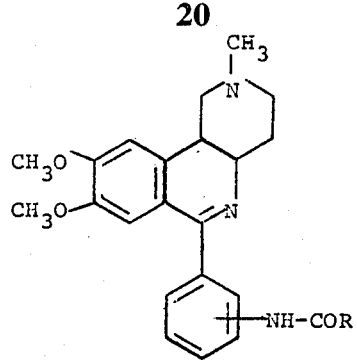

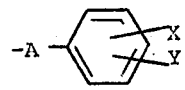

wherein
R is hydrogen, alkyl of 1 to 17 carbon atoms, thienyl, furyl, pyrrolyl, pyridyl or wherein
A is a direct bond, alkylene of 1 to 3 carbon atoms or vinylene,
X is hydrogen, alkyl of 1 to 4 carbon atoms, alkoxy of 1 to 4 carbon atoms, fluorine, chlorine or bromine, and
Y is hydrogen, alkyl of 1 to 4 carbon atoms or alkoxy of 1 to 4 carbon atoms.

13. The method of claim 11, wherein in the compound R₁ is hydrogen, alkyl of 1 to 3 carbon atoms, alkoxy of 1 to 3 carbon atoms or alkylthio of 1 to 3 carbon atoms, fluorine, bromine, chlorine, nitro, trifluoromethyl, amino or amido of 2 to 4 carbon atoms, R₂ is hydrogen, chlorine, alkyl of 1 to 3 carbon atoms or alkoxy of 1 to 3 carbon atoms, and R₃ and R₄ are both hydrogen or methoxy, or R₃ and R₄ together are methylenedioxy.

14. The method of claim 11, wherein the compound is cis-6-(4-acetamidophenyl)-1,2,3,4,4a,10b-hexahydro-8,9-dimethoxy-2-methyl-benzo[c][1,6]naphthyridine.

15. The method of claim 11, wherein the compound is cis-1,2,3,4,4a,10b-hexahydro-8,9-dimethoxy-2-methyl-6-phenyl-benzo[c][1,6]naphthyridine.

16. The method of claim 11, wherein the compound is administered at a daily dose of from about 0.1 to about 10 mg/kg animal body weight.

17. The method of claim 16, wherein the compound is administered at a daily dose of from about 10 mg to about 400 mg.

18. The method of claim 17, wherein the compound is orally administered in unit dosage form, containing from about 3 to about 200 mg of the compound.

19. The method of claims 18, wherein the compound is cis-1,2,3,4,4a,10b-hexahydro-8,9-dimethoxy-2-methyl-6-phenyl-benzo[c][1,6]naphthyridine.

20. The method of claim 18, wherein the compound is cis-6-(4-acetamidophenyl)-1,2,3,4,4a,10b-hexahydro-8,9-dimethoxy-2-methyl-benzo[c][1,6]naphthyridine.

* * * * *